United States Patent [19]

Shannahan

[11] Patent Number: 5,554,107
[45] Date of Patent: *Sep. 10, 1996

[54] ELASTIC FOOTWRAP

[76] Inventor: Donald R. Shannahan, 112 W. Logan, Caldwell, Id. 83605

[ * ] Notice: The term of this patent shall not extend beyond the expiration date of Pat. No. 5,460,601.

[21] Appl. No.: 481,763

[22] Filed: Jun. 6, 1995

Related U.S. Application Data

[62] Division of Ser. No. 27,187, Mar. 5, 1993, Pat. No. 5,460,601.

[51] Int. Cl.$^6$ ...................................................... A61F 13/00
[52] U.S. Cl. ........................ 602/66; 2/16; 36/91; 602/62; 602/65
[58] Field of Search ................. 602/61–66, 30; 36/4, 34 K, 93, 94, 11.5

[56] References Cited

U.S. PATENT DOCUMENTS

| | | | |
|---|---|---|---|
| 715,543 | 12/1902 | Bosworth | 602/30 |
| 822,138 | 5/1906 | Little . | |
| 982,664 | 1/1911 | Fisher . | |
| 1,365,512 | 1/1921 | Lewis . | |
| 1,406,583 | 2/1922 | Ruge . | |
| 1,512,218 | 10/1924 | Goldsmith . | |
| 1,772,179 | 9/1930 | Finkelstein | 602/30 |
| 2,237,652 | 4/1941 | Capezio | 36/94 |
| 2,515,903 | 7/1950 | Sjoquist | 602/66 |
| 2,561,836 | 6/1951 | Holm | 602/62 |
| 2,708,930 | 5/1955 | Lowman | 602/27 |
| 3,724,458 | 4/1973 | Piper | 602/62 |
| 4,084,586 | 4/1978 | Hettick . | |
| 4,085,745 | 4/1978 | Alenares . | |
| 4,476,858 | 10/1984 | Curtis | 602/62 |
| 4,550,511 | 11/1985 | Gamm | 36/91 |
| 4,597,395 | 7/1986 | Barlow et al. | 602/65 |
| 4,958,384 | 9/1990 | McCrane | 2/20 |
| 5,092,318 | 3/1992 | More et al. | 602/27 |
| 5,460,601 | 10/1995 | Shannahan | 602/66 |

Primary Examiner—Stephen R. Crow
Assistant Examiner—Kim M. Lee
Attorney, Agent, or Firm—Ormiston Korfanta Dunbar & Holland

[57] ABSTRACT

A footwrap comprising a modified tubular body of elastic material wherein the body has an ankle opening and a plurality of toe openings. The ankle opening is positioned to extend from above the heel forward along both sides of the foot just below the ankle to the top of the foot. The toe openings are positioned forward of the ankle opening so that the body envelops the foot between the ankle opening and the toe openings and exerts a predetermined compressive force to support the arch of the foot. The body is adapted to envelope the heel below the ankle opening to form a heel cup, the heel cup being positioned so that a predetermined compressive force is exerted along the bottom of the foot between the heel and the toes.

3 Claims, 6 Drawing Sheets

ELASTIC FOOTWRAP

CROSS REFERENCE TO RELATED APPLICATIONS

This is a divisional application of prior application Ser. No. 08/027,187, now U.S. Pat. No. 5,460,601, by D. Shannahan, filed Mar. 5, 1993, entitled Elastic Footwrap.

1. Field of the Invention

The invention relates generally to a device for supporting the foot and more particularly to a device for relaxing and shortening the musculatures of the foot to treat plantar fasciitis.

2. Background of the Invention

Plantar fasciitis is a common foot disorder that causes heel spur and other types of plantar facial pain. Plantar fasciitis can be treated, and the associated pain relieved, by shortening and relaxing the musculatures of the foot. The various elastic footwraps currently available typically provide only superficial support for the veins of the foot, the arch or the ankle joint. Such footwraps are not designed to nor do they shorten and relax the musculatures of the foot. Accordingly, it is one object of the invention to provide an elastic footwrap that effectively treats plantar fasciitis by shortening and relaxing the musculatures of the foot.

Plantar fasciitis is currently treated by wrapping the foot with tape or materials with tape-like backing. If done correctly, taping the foot can shorten and relax the musculatures of the foot to effectively treat plantar fasciitis and relieve the pain associated therewith. But taping must be done by a physician or other trained medical person and may not be removed and reinstalled by the patient. It is desireable to treat plantar fasciitis with a device that may be correctly used by the patient, including removal and reinstallation, to lower the cost of treatment and to minimize the incidental discomfort and inconvenience associated with taping (such as itching and difficulty bathing). Accordingly, it is another object of this invention to provide a device for treating plantar fasciitis that may be correctly removed and reinstalled by the patient.

Taping treats plantar fasciitis by fixing the foot in a predetermined position. Once the foot is taped, its position may not be adjusted with any significant degree of precision. Some adjustment is possible, but only by retaping the foot. Re-taping is time consuming and expensive. It is desireable that the device used to treat plantar fasciitis provide a means for accurately adjusting the position of the foot in an efficient and cost effective manner. Accordingly, another object of this invention is to provide a device for treating plantar fasciitis that allows for the adjustment of the position of the foot with a significant degree of precision in a way that is quicker and less costly than taping.

SUMMARY OF THE INVENTION

The above and other objects of the invention are achieved by a footwrap comprising a modified tubular body of elastic material. The body has an ankle opening and a plurality of toe openings. The ankle opening is positioned to extend from above the heel forward along both sides of the foot just below the ankle to the top of the foot. The toe openings are positioned forward of the ankle opening so that the body envelops the foot between the ankle opening and the toe openings and exerts a predetermined compressive force to support the arch of the foot. The body is adapted to envelope the heel below the ankle opening to form a heel cup, the heel cup being positioned so that a predetermined compressive force is exerted along the bottom of the foot between the heel and the toes.

BRIEF DESCRIPTION OF THE DRAWINGS

These and other features, aspects, and advantages of the invention will become better understood with regard to the following description, claims and accompanying drawings where:

DETAILED DESCRIPTION OF THE INVENTION

Figure 1:
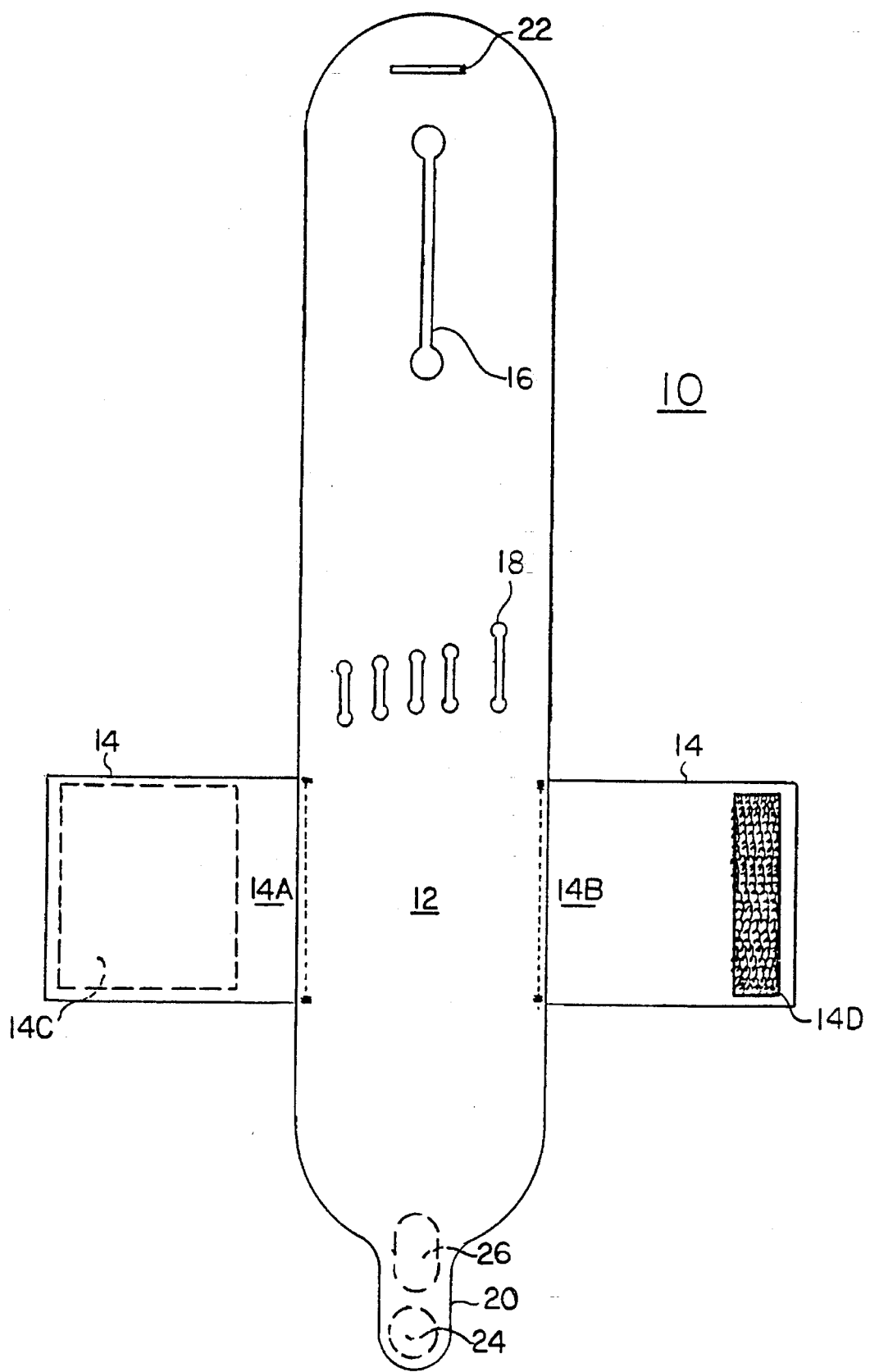
FIG. 1 shows a plan view of one embodiment of the footwrap.
Figure 2A:
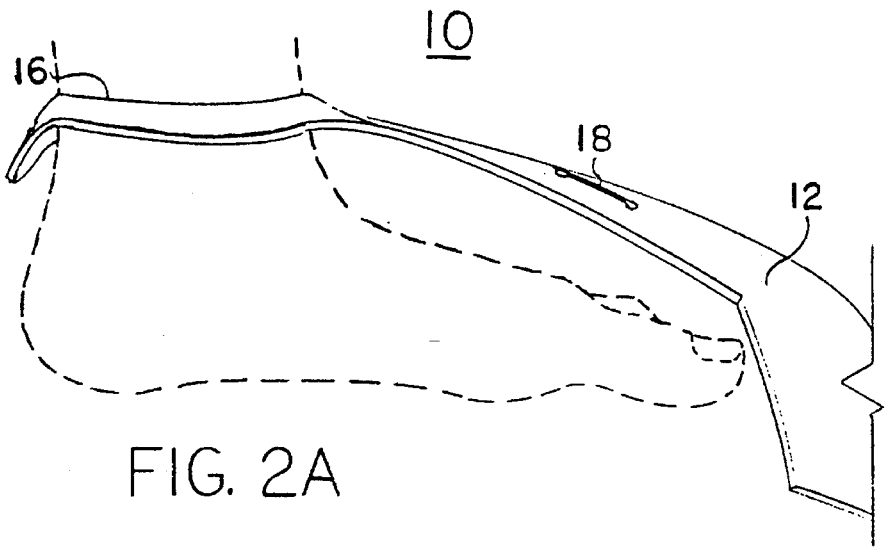
FIGS. 2A and 2B show the footwrap of FIG. 1 sequentially in various positions being installed on the foot.
Figure 2B:
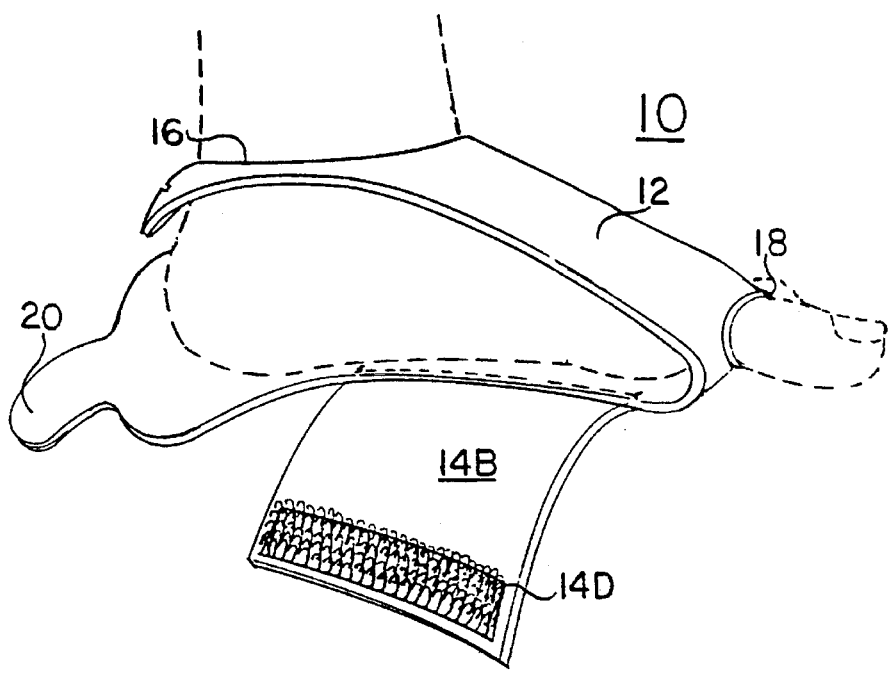
Figure 2C:
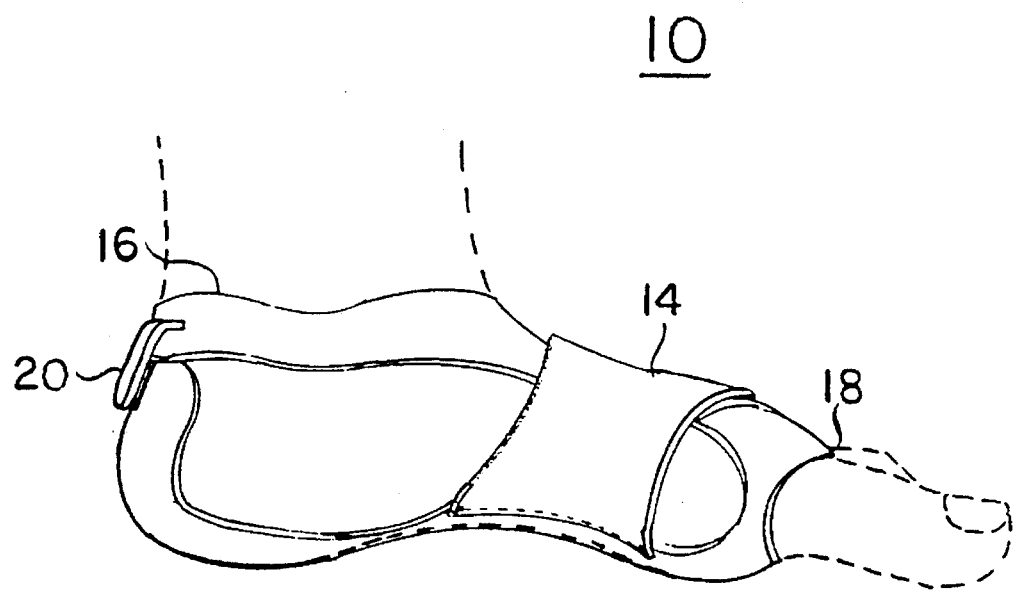
FIG. 2C shows the footwrap of FIG. 1 in operative position on the foot.

The preferred embodiment of the invention, illustrated in plan view in FIG. 1, is a footwrap 10 having a body 12 and an arch support 14. The body 12 is made of elastic material and is generally rectangular, being sized and proportioned to the individual foot. The body 12 has an ankle opening 16 and a plurality of toe openings 18. As illustrated in FIGS. 2A, 2B and 2C, the ankle opening 16 extends from above the heel at the lower part of the Achilles tendon forward along both sides of the foot below the protuberance of the ankle to the top of the foot just below the angle of the ankle. The toe openings 18 are positioned forward of the ankle opening 16 so that the toes may be inserted through the toe openings 18 when the footwrap is installed on the foot.

One end of the body forms a tongue 20 and the other end has a slot 22 therein for receiving the tongue 20 when the footwrap is installed on the foot. A patch 24 is attached to the end of the tongue 20. A complementary patch 26 is attached to the body 12 immediately in front of the tongue 20 to engage patch 24 when the tongue 20 is inserted through the slot 22. Patches 24 and 26 are made of synthetic materials that adhere when press together, commonly referred to under the trademark "VELCRO." The slot 22 is sufficiently wide to allow the tongue 20 to pass through it to secure the ends of the body 12 as shown in FIG. 2C.

Figure 1A:
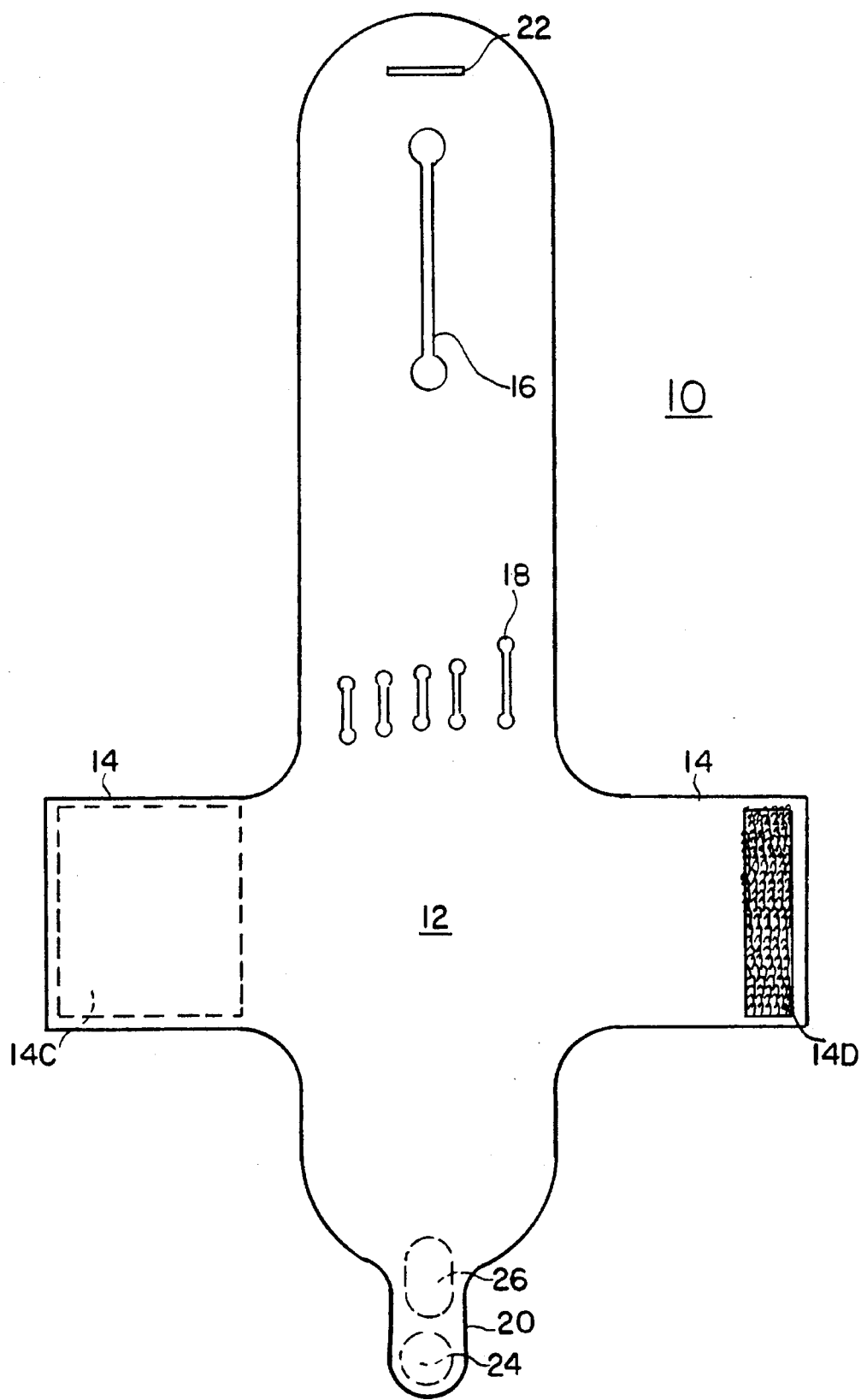
FIG. 1A shows a plan view of another embodiment of the footwrap.

The arch support 14 is made of elastic material and is generally rectangular, having a first end 14A and a second end 14B being sized and proportioned to the individual foot. The arch support 14 is positioned perpendicular to the body 12 between the toe openings 18 and the tongue 20 below the medial longitudinal arch of the foot. The first end 14A and the second end 14B are sewn to the body 12 so as to provide elasticity substantially the same as that of the elastic material. Alternatively, the arch support 14 and the body 12 may be a unitary piece of elastic material as shown on FIG. 1A. Complementary patches 14C and 14D are made of synthetic materials that adhere when pressed together, commonly sold under the trademark "VELCRO." Patches 14C and 14D are attached to the first end 14A and the second end 14B for securing the arch support 14 on the top of the foot.

If the footwrap is not made of ravel free material, then the borders of the body 12, arch support 14, ankle opening 16, toe openings 18, and slot 22 are finished so as to retard tearing or unraveling and to provide elasticity substantially the same as that of the elastic material.

Installation of the preferred embodiment of the footwrap is illustrated in FIGS. 2A, 2B and 2C. The footwrap 10 is installed on the foot by stepping through the ankle opening 16 and placing the toes through the toe openings 18 as shown in FIGS. 2A and 2B. The tongue 20 is then inserted into and drawn through the slot 22 until the desired compressive force is exerted along the bottom of the foot between the heel and the toes. The ends of the body are secured by meshing the "VELCRO" patch 24 on the tongue 20 with the complementary "VELCRO" patch 26 on the body 12 as illustrated in FIG. 2C. The arch support 14 is drawn around and over the lateral and medial sides of the foot and attached to the top of the body 12 by meshing the "VELCRO" patches 14C and 14D as illustrated in FIG. 2C. The arch support 14 is cinched up as necessary to provide the desired support for the arch-of the foot. When the footwrap is in the operative position on the foot, the body 12 exerts a compressive force of predetermined magnitude along the bottom of the foot, using the heel of the foot as a fulcrum and the forefoot as a base, to relax and shorten the musculatures of the foot. The magnitude of the compressive force along the bottom of the foot can be adjusted by varying the length of tongue 20 that is inserted through the slot 22. The magnitude of this compressive force can also be adjusted by varying the elasticity of the material forming the body 12. The desired support for the arch of the foot is achieved by cinching up the arch support 14 and securing on top of the foot. The support for the arch may be adjusted by varying the length of overlap of the first end 14A and the second end 14B. The support of the arch may also be adjusted by varying the elasticity of the material forming the arch support 14.

Figure 3:
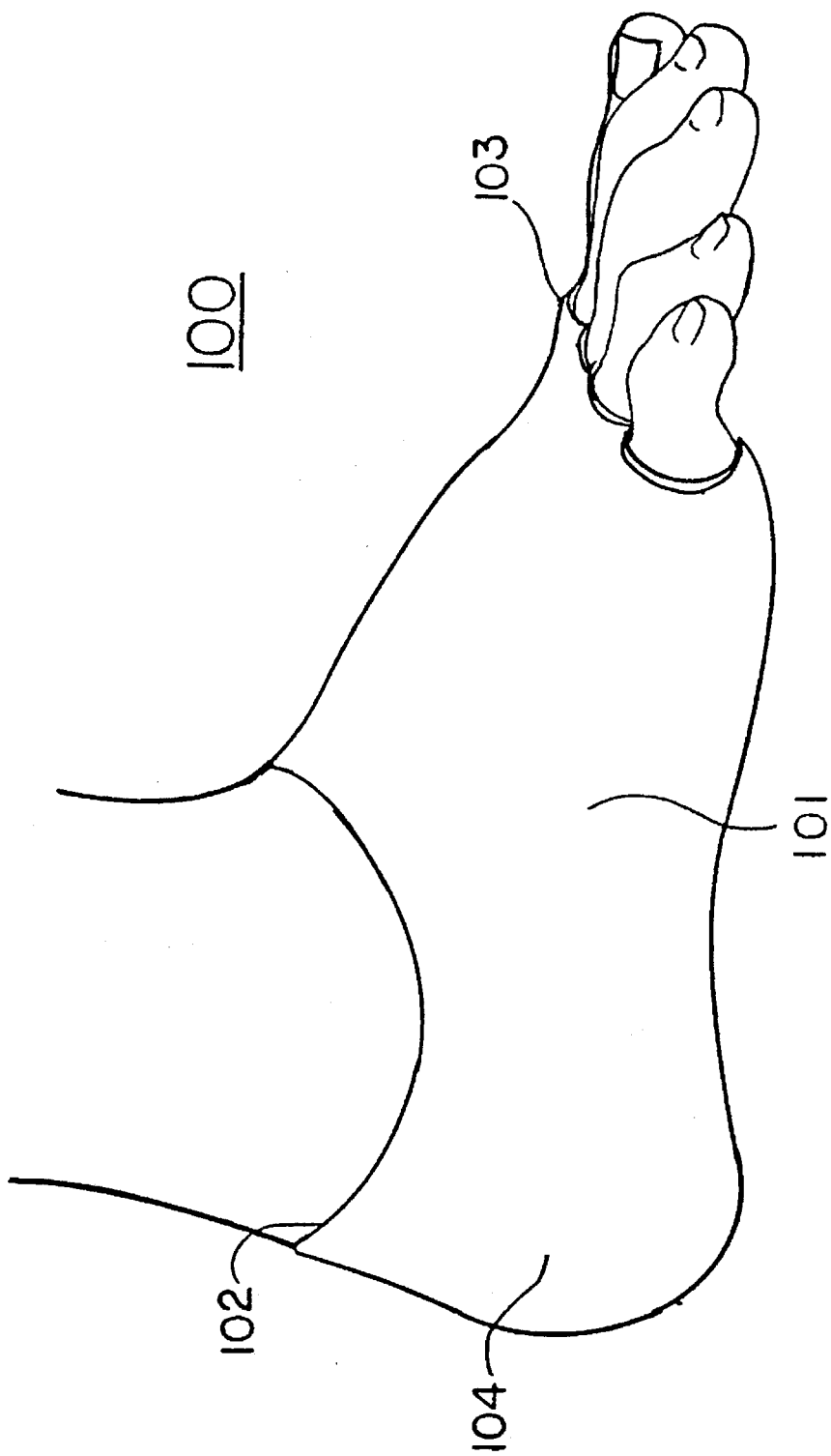
FIG. 3 shows another embodiment of the footwrap in operative position on the foot.
Figure 3A:
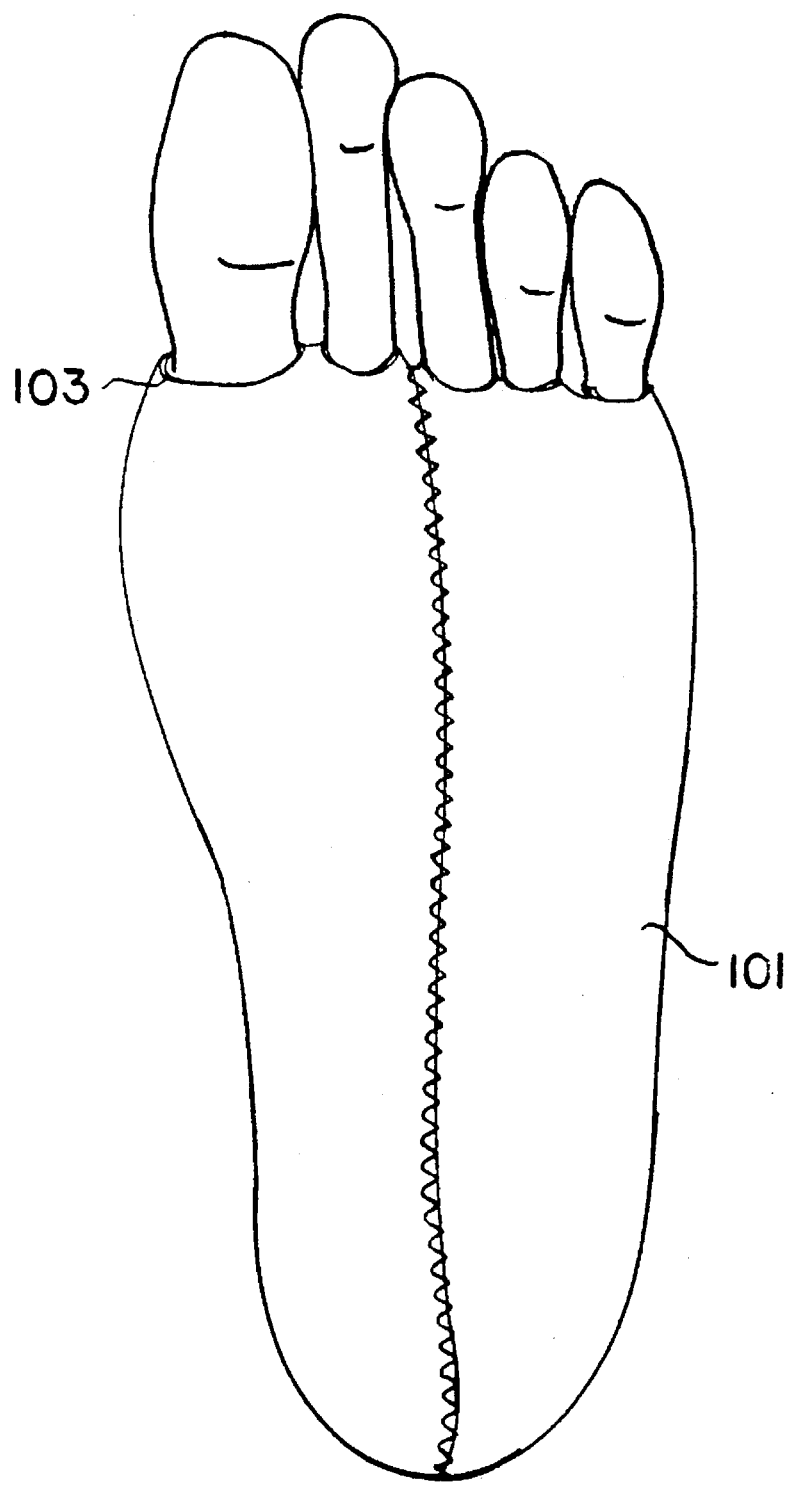
FIG. 3A shows the footwrap of FIG. 3 with a seam extending along the bottom of the foot and the rear of the heel.

The preferred embodiment of the footwrap achieves the several objects of the invention and is well suited for practical use. Other embodiments of the footwrap might be made. For instance, FIGS. 3 and 3A illustrate another embodiment of the footwrap 100 having a modified tubular body 101 made of elastic material with an ankle opening 102, toe openings 103 and a heel cup 104. The body 101 may be constructed as a unitary seamless piece of elastic material, as shown in FIG. 3, or from a sheet of elastic material folded substantially in half and joined in a seam extending along the bottom of the foot and the rear of the heel, as shown in FIG. 3A. This embodiment of the footwrap envelops the foot from the heel to the toes and exerts a predetermined compressive force to support the arch of the foot and along the bottom of the foot to shorten and relax the musculatures of the foot.

I claim:

1. An elastic footwrap for treating plantar fasciitis, which comprises:

a. a tubular body of elastic material, the body having an ankle opening and a plurality of toe openings;

b. the ankle opening being positioned to extend from above the heel forward along both sides of the foot just below the ankle to the top of the foot;

c. the toe openings being positioned forward of the ankle opening so that the body envelops the foot between the ankle opening and the toe openings and exerts a predetermined compressive force to support the arch of the foot; and d. the body being adapted to envelope the heel below the ankle opening to form a heel cup, the heel cup being positioned so that a predetermined compressive force is exerted along the bottom of the foot between the heel and the toes.

2. The footwrap of claim 1, wherein the body is constructed as a unitary seamless piece of elastic material.

3. The footwrap of claim 1, wherein the body is constructed from a sheet of elastic material folded substantially in half and joined in a seam extending along the bottom of the foot and the rear of the heel.

\* \* \* \* \*